United States Patent
Li et al.

(10) Patent No.: US 10,089,436 B2
(45) Date of Patent: Oct. 2, 2018

(54) METHOD AND APPARATUS FOR CALLING SINGLE-NUCLEOTIDE VARIATIONS AND OTHER VARIATIONS

(71) Applicant: AccuraScience, LLC, Johnston, IA (US)

(72) Inventors: Tongbin Li, Johnston, IA (US); Wuming Gong, Saint Paul, MN (US); Jiang Rao, Beijing (CN)

(73) Assignee: ACCURASCIENCE, LLC, Johnston, IA (US)

( * ) Notice: Subject to any disclaimer, the term of this patent is extended or adjusted under 35 U.S.C. 154(b) by 98 days.

(21) Appl. No.: 14/358,643

(22) PCT Filed: Feb. 13, 2014

(86) PCT No.: PCT/CN2014/072043
§ 371 (c)(1),
(2) Date: May 15, 2014

(87) PCT Pub. No.: WO2015/062184
PCT Pub. Date: May 7, 2015

(65) Prior Publication Data
US 2016/0026757 A1      Jan. 28, 2016

Related U.S. Application Data

(60) Provisional application No. 61/898,680, filed on Nov. 1, 2013.

(51) Int. Cl.
| G06F 19/22 | (2011.01) |
| G06F 19/18 | (2011.01) |
| G06F 19/24 | (2011.01) |

(52) U.S. Cl.
CPC .............. *G06F 19/22* (2013.01); *G06F 19/18* (2013.01); *G06F 19/24* (2013.01)

(58) Field of Classification Search
None
See application file for complete search history.

(56) References Cited

U.S. PATENT DOCUMENTS

| 6,274,320 B1 | 8/2001 | Rothberg et al. |
| 8,392,126 B2 | 3/2013 | Mann |

FOREIGN PATENT DOCUMENTS

| CN | 101390101 A | 3/2009 |
| CN | 102206704 A | 10/2011 |
| CN | 102952855 A | 3/2013 |
| CN | 103114150 A | 5/2013 |
| WO | WO-2010127045 A2 | 11/2010 |

OTHER PUBLICATIONS

"International Application Serial No. PCT/CN2014/072030, International Search Report dated Aug. 4, 2014", 4 pgs.
"International Application Serial No. PCT/CN2014/072030, Written Opinion dated Aug. 4, 2014", 4 pgs.
"International Application Serial No. PCT/CN2014/072043, International Search Report dated Aug. 13, 2014", 4 pgs.
"International Application Serial No. PCT/CN2014/072043, Written Opinion dated Aug. 13, 2014", 4 pgs.
"Phred Quality Score", Wikipedia, (Accessed Aug. 15, 2013), 4 pgs.
Ewing, Brent, et al., "Base-Calling of Automated Sequencer Traces Using Phred. I. Accuracy Assessment", Genome Research 8, (1998), 175-185.
Ewing, Brent, et al., "Base-Calling of Automated Sequencer Traces Using Phred. II. Error Probabilities", Genome Research 8, (1998), 186-194.
Hoggart, C. J, et al., "Simultaneous Analysis of All SNPs in Genome-Wide and Re-Sequencing Association Studies", PLoS Genetic, vol. 4, No. 7, (Jul. 25, 2008), 8 pgs.
Lijavetzky, Diego, et al., "High throughput SNP discovery and genotyping in grapevine (*Vitis vinifera* L.) by combining a re-sequencing approach and SNPlex technology", BMC Genomics, vol. 8, No. 424, (Nov. 19, 2007), 11 pgs.

*Primary Examiner* — Joseph Woitach
(74) *Attorney, Agent, or Firm* — Zheng Liu; Weintraub Tobin

(57) ABSTRACT

Base calls for a target sequence may be identified relative to a reference sequence by using values from sequencing reads at locations satisfying a high-confidence condition to identify base calls at a given location not satisfying the high-confidence condition. The high-confidence condition may relate to the level of coverage by the sequencing reads at a location of the reference sequence. The quality of measurements of the sequencing reads may be incorporated into the base-call process.

8 Claims, 6 Drawing Sheets

METHOD AND APPARATUS FOR CALLING SINGLE-NUCLEOTIDE VARIATIONS AND OTHER VARIATIONS

CROSS-REFERENCE TO RELATED APPLICATIONS

This application is a continuation of U.S. patent application Ser. No. 14/358,643, filed May 15, 2014, which is a U.S. National Stage Application under 35 U.S.C. § 371 of PCT/CN2014/072043, filed Feb. 13, 2014, which claims the benefit of U.S. Provisional Application No. 61/898,680, filed Nov. 1, 2013. All above-identified patent applications are hereby incorporated by reference in their entireties.

FIELD

The present disclosure relates generally to nucleotide data and more particularly to data processing for nucleotide data.

BACKGROUND

Applications related to the comparison of a target sequence of nucleotide data to a reference sequence of nucleotide data typically have limited ability to account for the effects of data coverage and data quality. Thus, there is a need for improved methods and related systems to compare a target sequence to a reference sequence.

BRIEF DESCRIPTION OF DRAWINGS

Some embodiments are illustrated by way of example and not limitation in the figures of the accompanying drawings.

FIGS. 3A, 3B, and 3C are diagrams that show tables related to the embodiment of FIG. 1.

FIG. 4 is a flowchart that shows a sampling method related to the embodiment of FIG. 1.

FIG. 5 is a flowchart that shows another sampling method related to the embodiment of FIG. 1.

DETAILED DESCRIPTION

1. Background

Figure 1:
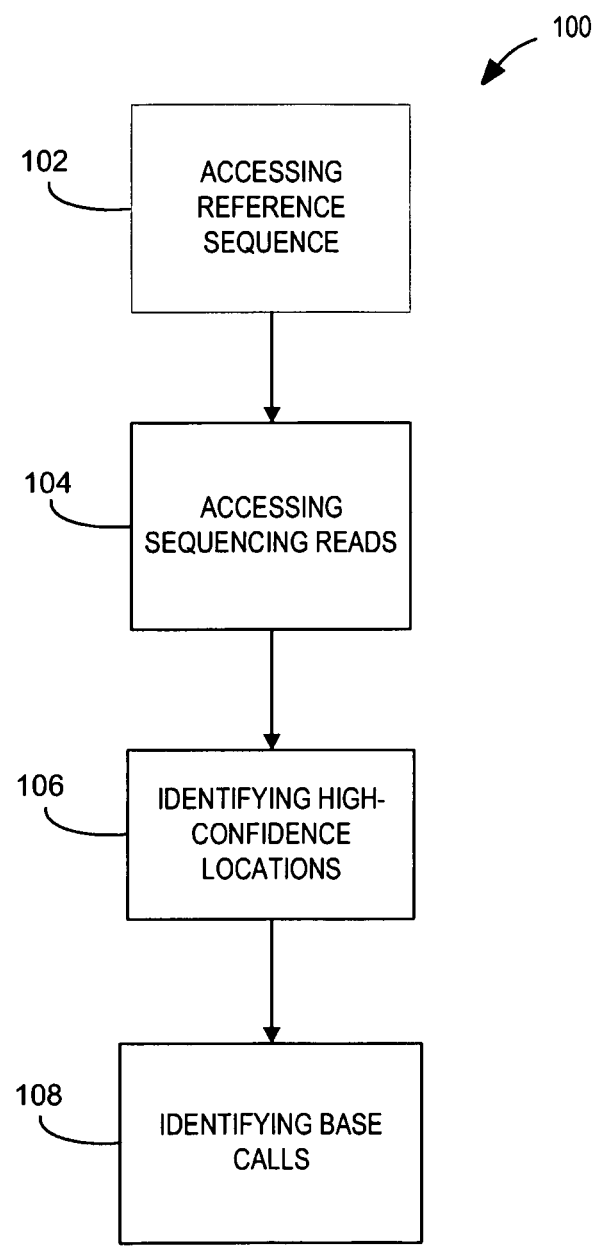
FIG. 1 is a flowchart that shows a method of identifying at least one base call for a target sequence according to an example embodiment.

With the substantial advances of next-generation sequencing technologies, researchers have found multiple ways to take advantage of these technologies and developed multiple applications. One important use or application of the next-generation sequencing technologies/data is the so-called re-sequencing application, that is, the sequencing experiment is performed for the purpose of generating data that can be mapped to a reference sequence, and the experiment is conducted for the purpose of finding the difference between the newly generated sequence (e.g., one's own genome sequence) and the reference sequence (e.g., the human reference genome, resulting from the Human Genome Project completed about a decade ago). Re-sequencing application can further be split into whole-genome sequencing and targeted re-sequencing, and the latter further split into exome sequencing (that is, the sequencing of all ~20,000 protein-coding genes of an individual) and other, more specialized targeted sequencing (e.g., sequencing of a selected subset, or "panel", of protein-coding genes that present risks of, say, prostate cancer).

Single-nucleotide variation (SNV) calling is a critical step in a typical analysis pipeline for re-sequencing applications. It refers to the calling (or determining) of single-base differences between a newly generated sequence and a reference sequence. Besides SNVs, there are two other common types of variations between an individual sample's sequence and the reference sequence: (1) Indels (e.g., insertions or deletions, possibly including a stretch of changes up to 50 nucleotides long), and (2) structural variations (SVs) or copy number variations (CNVs), which may include changes involving very long stretches—thousands or even millions of nucleotides. Conventionally an indel (or Indel, InDel) is understood as either an insertion or a deletion at a given location with the plural form indels (or Indels, InDels). Although the calling of these two latter types of variants is generally more difficult than the calling of SNVs, the present disclosure may be applied to these variations also as will be clear to those skilled in the relevant art.

Variant calling, including SNV calling, indel calling and SV or CNV calling, follows a mapping or alignment step in the analysis pipeline. Mapping or alignment refers to the operation by which the original sequencing reads are mapped to the reference sequence. Because the sequencing reads are short, and there are many repeated regions in the very long reference sequence (e.g., the human reference genome is 3-4 billion nucleotides long), finding the precise position in the reference sequence where a read is mapped to is also challenging. Mapping methods, which are known to those skilled in the art, are not discussed here.

One reason SNV calling is difficult for next-generation sequencing (NGS) is because the error rate produced by conventional NGS technologies (e.g., ILLUMINA Technology) is commonly believed to be on the level of 1%, which is one order of magnitude higher than the SNV rate (that is, the proportion of nucleotides that are different between any two individuals, or between one's genome and the reference genome). Both SNVs and sequencing errors are reflected as differences between the sequencing data and the reference sequence. In other words, the "noise" (e.g., sequencing error) is one order of magnitude higher than the "signal" (e.g., real SNVs).

To some extent, this difficulty can be countered by a deep sequencing strategy whereby each region or each position is covered by many reads, so that certain statistical methods (e.g., Bayesian-based modeling) can be applied to more reliably determine whether the difference seen between an individual's sequence and the reference sequence is due to sequencing errors, which can be resolved by averaging, or real SNVs, which occur systematically. However, conventional statistical methods including Bayesian-based modeling have been limited in their ability to incorporate the individual's sequence data into relevant statistical characterizations (e.g., prior and conditional probabilities). Instead these statistical characterizations are typically based on some assumed "general behavior" of SNVs individual's sequence data.

2. Method Embodiment

Example methods and systems are directed to data processing for nucleotide data. The disclosed examples merely typify possible variations. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

For the purpose of this discussion of SNV calling, we use the two terms "SNV calling" and "genotyping" interchangeably. We also assume the individual being sampled is a diploid (that is, has two slightly different copies of DNA mapping to each region of the reference sequence, one inherited from the individual's father, the other from his/her mother), though the methods described herein are equally applicable to samples with a different ploidy. We want to call the diploid genotype of each position in the reference sequence that is covered by the newly generated sequencing data. Because there are four possible nucleotides for each position on each of the two copies of the DNA, there are a total of 10 possible diploid genotypes: AA, CC, GG, TT—these 4 are called homozygous genotypes, and AC, AG, AT, CG, CT, GT—these 6 are called heterozygous genotypes—these are self-explanatory.

Because the sampled individual and the reference sequence are of the same species, they are very similar. In fact, for the human species, on average they differ in only ~0.1% of the positions. (Thus, as noted above, this rate of difference is one order of magnitude lower than the sequencing error rate (~1%).) Considering the large size of the reference sequence (billions of bases), we are looking at a few million positions of differences between the new sequence and the reference sequence, in case of whole-genome re-sequencing. It should also be noted that since the reference sequence is haploid (i.e., one copy per position), we want to identify the difference between a diploid individual's sequence and a haploid reference sequence. Consequently, the identified differences can be further categorized as homozygous SNVs (e.g., the reference is A, and the individual's genotype is CC) and heterozygous SNVs (e.g., the reference is A, and the individual's genotype is AC). There are rare occasions where 3 bases are involved in a position (e.g., the reference is A, but the individual's genotype is CG); however, these rare occasions are not commonly considered. For a non-human species (e.g., pig) whose inter-individual variation level may be higher or whose reference genome may have a quality problem, this situation (e.g., a position is heterozygous, but both nucleotides are different from the reference base) may occur more frequently. The embodiments described in this disclosure are equally applicable for these situations.

As described below, the statistical characteristics of the SNV-calling process are affected by both the quality and the coverage of the measurements.

Sequencing read data generated from next-generation sequencing equipment include a string of n bases (n is the read length, an integer typically between 50 and 150) from the 4-character alphabet {A, C, G, T}. Each character in this string is called a "base call", corresponding to a position in the read. In addition, each base (or position) in each read is associated with a quality score, called Phred score, which is produced by the sequencing machine, and it represents the confidence about the accuracy of the "base call". The Phred score is calculated as $-10 \cdot \log_{10}$ (error rate). So, a Phred score of 20 represents an estimated error rate of 0.01, and a Phred score of 30 represents an estimated error rate of 0.001.

As discussed above, next-generation sequencing typically produces short reads but has very high throughput, so a "deep sequencing" strategy is applied; that is, each region is sequenced many times over, and thus each position is covered by multiple reads. Let's use L to represent the "depth coverage" of the position of interest. For our practice, we will attempt to make a SNV call (or genotyping) for each position with depth L where at least 1 of the L reads shows a different base call from the base in the reference sequence. These are called "dubious positions" in our discussion. Because we do not consider situations where 3 bases are involved in a position (as discussed above), given that we know the nucleotide identity in the reference sequence for a particular "dubious position"—let's call this nucleotide in the reference sequence R, there is at most one other nucleotide involved in the sequencing data for this position—let's call it N. Although in theory there are 10 possible diploid genotypes for each position, once R and N are fixed, only 3 diploid genotypes are possible: RR, NN (these are the two homozygous genotypes), and RN (this is the heterozygous genotype).

Certain embodiments combine statistical characteristics based on quality scores associated with sequencing machines and the depth level of the sequencing strategy. By combining these statistical effects, these embodiments enable the characterization of high-confidence locations in in the sequencing reads where base values can be used to identify base calls at other locations.

Figure 2:
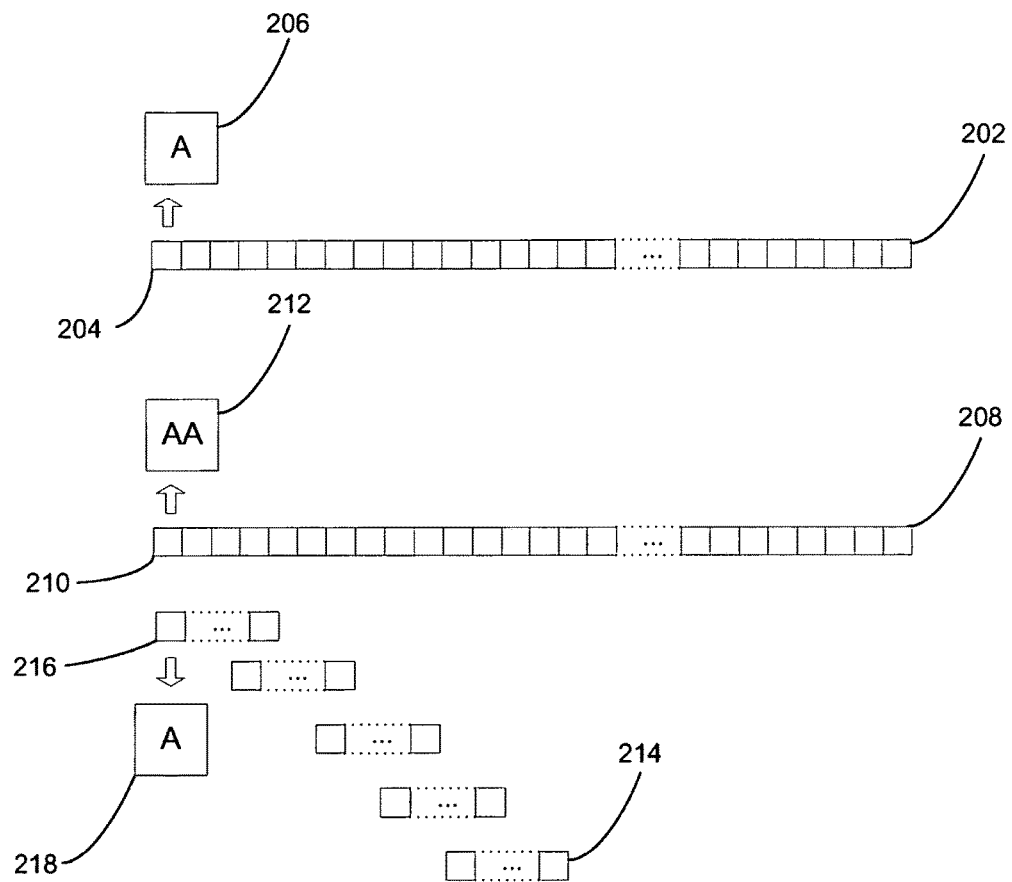
FIG. 2 is a diagram that shows sequence elements related to the embodiment of FIG. 1.

FIG. 1 shows a method 100 of identifying at least one base call for a target sequence 208 that is shown in FIG. 2 for an example embodiment. A first operation 102 includes accessing the reference sequence 202, the reference sequence 202 including a plurality of base values that define the reference sequence. For example, the reference may a portion of a known genome characterized as a sequence of base values (e.g., "ACACTG . . . "), where the length may be arbitrarily long (e.g., 3-4 billion base values for the human genome). In FIG. 2, a first element 204 of the reference sequence 202 includes the base value A as shown at block 206, and a first element 210 of the target sequence 208 includes the base values AA as shown at block 212 for a diploid subject.

A second operation 104 includes accessing a plurality of sequencing reads 214, each sequencing read 214 including a plurality of base values for a corresponding portion of the target sequence 208. The sequencing reads 214 may be characterized as a sequence of base values (e.g., "ACACTG . . . "), where the lengths may be 50-150 base values or some arbitrary range. These sequence reads 214 may correspond to genomic data produced by a genomic measurement system. In FIG. 2, a first element 216 of a first one of the sequencing reads 214 includes the base value A as shown at block 218. As will be appreciated by one skilled in the art, the relative alignments of the target sequence 208 and the sequencing reads 214 is illustrated by the horizontal axis in FIG. 2, so that each entry of the target sequence 208 or one of the sequencing reads 214 corresponds to a location of the reference sequence 202.

A third operation 106 includes identifying a plurality of high-confidence locations in the sequencing reads, a high-confidence location being identified with a corresponding location in the reference sequence and satisfying a high-confidence condition for using base values of the sequencing reads at the high-confidence location to identify one or more base calls for the target sequence at the high-confidence location. For example, the high-confidence condition may be satisfied at the high-confidence location if at least a threshold number of the sequencing reads include the high-confidence location and if a distribution of sequencing-read base values at the high-confidence location satisfies a statistical confidence criterion.

The high-confidence condition may be associated with a depth-level of coverage by the sequencing reads for a location in the reference sequence. For example, the each base value in a sequencing read may be associated (via a mapping) with a corresponding location in the reference sequence. The total coverage at that corresponding location may be described as the depth level at that location, where the depth level may vary from a relatively low depth level L (e.g., L<50) to a relatively high depth level H (e.g., H>50).

In accordance with certain embodiments as described below (e.g., FIGS. 3A-3C), sequencing-read values for locations at lower depth levels L may be extracted from sequencing-read values for locations at higher depth levels H. It is well known that the depth coverage of a sequencing dataset varies across regions. For higher depth regions (e.g., H>50), high confident SNV calling can be achieved no matter what SNV calling method is used. The challenge is in the lower depth regions. For regions of higher depth levels (e.g., H>50), we apply a set of filters to retain the positions whose genotypes are most confidently determined (e.g., if less than 5% of the H reads support N, the genotype is determined to be RR; if greater than 95% of the H reads support N, the genotype is determined to be NN, and if between 45 and 55% of the H reads support N, the genotype is determined to be RN).

Then for locations with lower depth levels L, a number of values from the higher depth levels H may be sampled. In general the sampling order M need not be identical to the depth level L, but the depth level may be used for the sampling order M so that M=L values are sampled. In order to capture the effects of the measurement quality associated with measurement system, the values may be further distinguished based on quality scores.

Figures 3A, 3B:
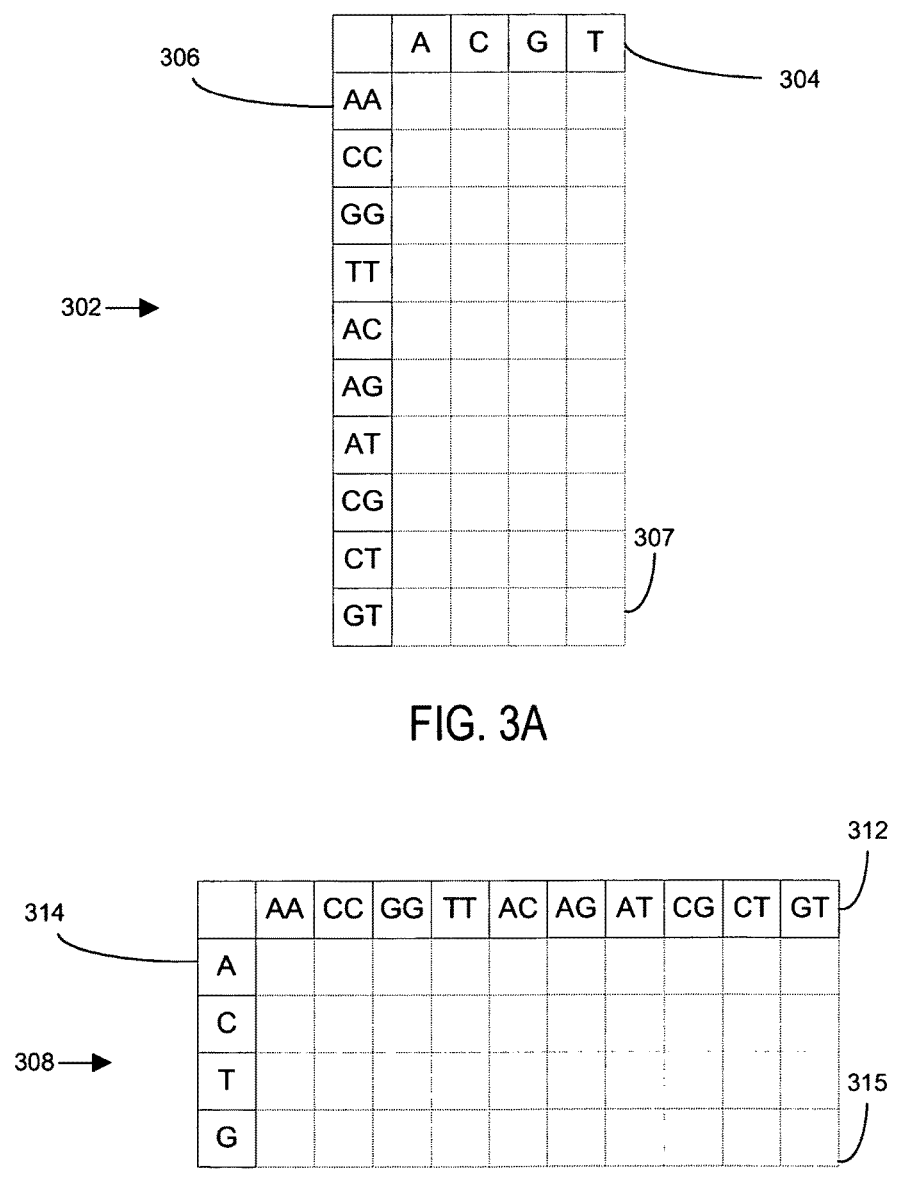
Figures 3C, 4, 5:
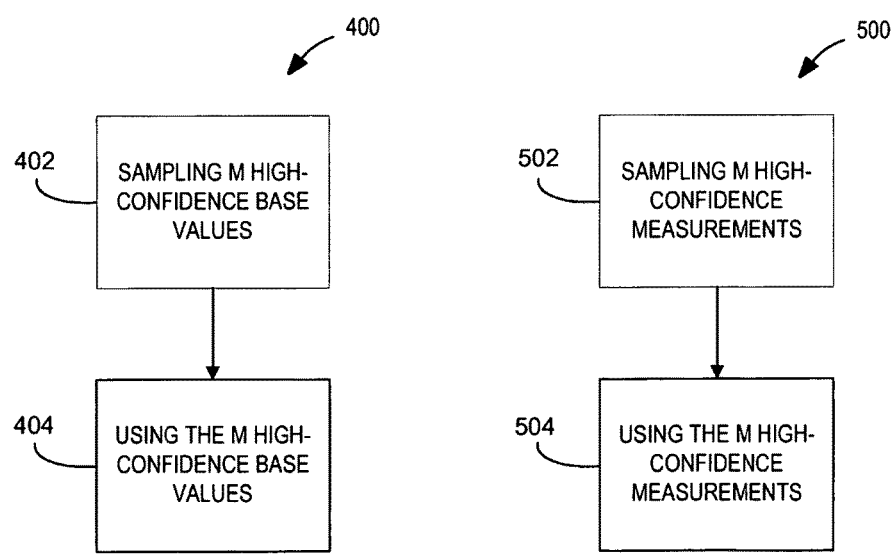

FIGS. 3A-3C show tables for an example embodiment that illustrates the use of depth levels and quality scores to characterize and separate data from the sequencing reads. In FIG. 3A, an SNV table 302 has a row index 304 for the four individual base values (A, C, G, T) that may occur at a location of the reference sequence and a column index 306 for the ten diploid combinations (AA, CC, GG, TT, AC, AG, AT, CG, CT, GT) that may occur at that location in one of the sequencing reads. Each cell 307 of the SNV table 302 provides a probability (e.g., likelihood) that a particular reference-sequence base value corresponding to the row index 304 results in a diploid combination corresponding to the row index 304 in the target sequence 208 corresponding to the sequencing reads 214. That is, the SNV table 302, which is derived from the sequencing-read values and reference-sequence values, may be used to predict the target sequence diploid values at a location based on the reference-sequence value at that location. Thus, the SNV table 302 may be described as a target-sequence prediction table.

Initially, the SNV table 302 may be constructed from high-confidence locations in the reference sequence, with a sufficiently high depth level (e.g., H>50) for coverage from the sequencing reads. Then, in order to account for limited data at lower depth levels L for some location in the reference sequence (e.g., as covered by values from the sequencing reads), one can construct a corresponding SNV table 302 indexed for a depth level L by sampling from high-confidence values that correspond to higher depth levels (e.g., H>50). FIG. 4 shows a related sampling method 400. A first operation 402 includes sampling M high-confidence base values from the sequencing reads for some positive integer M, the M high-confidence base values corresponding to at least one high-confidence location where a base value of the reference sequence is equivalent to a base value of the reference sequence at the given location. For example, in the case of sampling for a depth level L, one may take M=L. A second operation 402 includes using the M high-confidence base values to estimate a likelihood of the one or more target-sequence base values at the given location.

FIGS. 3B-3C show related error tables 308, 310 that characterize measurement predictions and related errors, where a first error table 308 corresponds to high-quality reads from a measurement system (e.g., based on Phred score thresholds) and where a second error table 310 corresponds to low-quality reads. That is, in order to evaluate the high-confidence condition, the sequencing reads may be split the sequencing data to two sub-populations—high-quality reads in the first table 308 and low-quality reads in the second table 310, if the data are produced from a conventional platform (e.g., an ILLUMINA platform) It should be noted that the disclosed embodiments can also be applied to next-generation sequencing data produced from other platforms (e.g., ION TORRENT) where there is no apparent sub-population quality split, in which case, this step may be omitted. A read may be classified as a high-quality read if the Phred score of each position within the read is above a certain level (default level is 15, but other values such as 20, 25 etc. can also be used). All other reads are classified as low-quality reads. It should be noted that although this embodiment employs a Phred score, alternative quality characterizations may be employed based on the operational setting.

The first error table 308 has a column index 312 that corresponds to the ten diploid combinations (AA, CC, GG, TT, AC, AG, AT, CG, CT, GT) that may occur at a location of the target sequence and a row index 314 that corresponds to the four individual base values (A, C, G, T) that may be identified by the measurement system for that location. Similarly the second error table 310 has a column index 316 that corresponds to the ten diploid combinations (AA, CC, GG, TT, AC, AG, AT, CG, CT, GT) that may occur at a location of the target sequence and a column index 318 that corresponds to the four individual base values (A, C, G, T) that may be identified by the measurement system for that location. Each cell 315, 319 of the error tables 308, 310 provides a probability (e.g., likelihood) that a particular a diploid combination corresponding to the column index 312, 316 results in a measurement corresponding to the row index 314, 318.

As in the case of the SNV table 302, the error tables 308, 310 may be first characterized at high depth levels (e.g., H>50) and then sampled for low depth levels. That is, the error rates for each level L are similarly calculated based on the positions whose genotypes are most confidently determined—followed by randomly sampling of L out of the H reads. Any base calls that are consistent with the genotype are assumed to be correct (e.g., a base call of A is considered to be correct if the genotype of the position is determined to be AA, or AC, or AG, or AT), and any base calls that are inconsistent with the genotype indicate a sequencing error. For multiple quality-level sequencing data (e.g., ILLUMINA data), the error rates are calculated for high- and low-quality reads separately, producing two error tables. For other sequencing platforms, only one error table is produced.

That is, in order to account for limited data at lower depth levels L for some location in the reference sequence (e.g., as covered by values from the sequencing reads), one can construct corresponding error tables 308, 310 indexed for a depth level L by sampling from high-confidence values that correspond to higher depth levels (e.g., H>50). FIG. 5 shows a related sampling method 500. A first operation 502 includes sampling M high-confidence measurements of the one or more target-sequence base values at the given location for some positive integer M, the M high-confidence measurements including base values from at least one high-confidence location where corresponding sequencing reads identify a combination of base values that is equivalent to the one or more target-sequence base values at the given location. For example, in the case of sampling for a depth level L, one may take M=L. A second operation 502 includes using the M high-confidence measurements with the one or more target-sequence base values at the given location to estimate a likelihood of the base values from the sequencing reads at the given location.

It should be emphasized that, in the embodiment we focus on, we assume diploid samples, but the procedure can be naturally extended to other ploidy situations (haploid, tetrapoid) without difficulty. For a given depth level L, each of the tables table 302, 308, 310 in FIG. 3A-3C contains 40 parameters extracted from higher depth regions (H) of the sequencing data, calculated for regions of lower depth (L). The base-wise SNV table shows the occurring rates of SNVs—that is, the real difference between the individual's genotype and the reference sequence. The values (or parameters) in the SNV table 302 will be used in the calculation of the prior probabilities for the diploid genotypes as discussed below. The error tables 308, 310 show the occurring rates of sequencing errors—produced by sequencing instrument. The values or parameters in the two error tables (one for high-quality reads and the other for low-quality reads). It should be noted that for platforms that do not generate two quality levels of reads (e.g., non-ILLUMINA platforms) there will be only one error table 308 for use in subsequent calculations as described below.

To summarize, each of the tables 302, 308, 310 of FIGS. 3A-3C is defined for each L level. Each column 304 in the SNV table 302 represents one of the four bases in the reference sequence 202, and each row 306 represents one of the ten possible real diploid genotypes in the target sequence 208 of the sequenced individual. Each cell of the SNV table 302 represents the probability that the corresponding diploid genotype occurs on a position with the specified reference base. Each column 312 in an error table 308 represents one of the ten diploid genotypes, and each row represents the base call produced by the sequencing instrument. There are two error tables 308, 310 for a conventional instrument with two quality levels (e.g., an ILLUMINA instrument)—one for high-quality reads and the other for low-quality reads. For other sequencing platforms, there is only one error table 308 as discussed above.

A fourth operation 108 in FIG. 1 includes identifying one or more base calls for the target sequence at a given location not satisfying the high-confidence condition by using base values of the sequencing reads at the high-confidence locations with base values of the sequencing reads at the given location and a base value of the reference sequence at the given location to identify the one or more base calls for the target sequence at the given location. For example, the target sequence may correspond to an N-ploid genotype and N base calls may be identified at the given location for some positive integer N.

The given location may be selected by determining that at least one sequencing read that includes the given location indicates an SNV relative to the reference sequence (e.g., a dubious position relative to the reference sequence). Additionally or alternatively, the given location may be selected by identifying an insertion or a deletion at the given location, a copy-number variation at the given location, or a structural variation at the given location.

A Bayesian prediction model may be used to identify the one or more base calls for the target sequence at the given location, the Bayesian prediction model providing likelihood values that relate the base values of the sequencing reads at the high-confidence locations and the base values of the reference sequence at multiple locations with the one or more base calls for the target sequence at the given location. For example, Identifying the one or more base calls for the target sequence at the given location may include using the base values of the sequencing reads at the high-confidence locations to evaluate likelihoods of combinations of the base value of the reference sequence at the given location and one or more base values for the target sequence at the given location. Further, identifying the one or more base calls for the target sequence at the given location may include using the base values of the sequencing reads at the high-confidence locations to evaluate likelihoods of combinations of one or more base values for the target sequence at the given location and a base call for the target sequence at the given location.

If we ignore the rare cases where a heterozygous genotype occurs and both bases are different from the reference base (e.g., reference base is 'A' but the genotype is "GC"), then we can partition the all positions at each L level into twelve partitions based on R:N combinations, then assign prior probabilities for each diploid genotype based on the relevant SNV tables 302. In the more general case, where we consider all ten diploid genotypes for each position, we can partition the positions into four categories based on the reference base, after which, we assign the prior probability for each of the 10 diploid genotypes for each of four categories.

As a result, the SNV table 302 (or tables) may be used to characterize a prior probability P(GT|R) or likelihood for any genotype GT (e.g., the column 5 index 306) for a given reference base value R (e.g., from the row index 304). Next the error tables 308, 310 may be used to characterize a conditional probability P(D|GT) or likelihood for measured sequencing data D (e.g., from the row indices 308, 310) for a given genotype GT (e.g., the column indices 312, 316) through the multinomial distribution:

$$P(D\mid GT) = \frac{L!}{l_R!l_N!(m-l_R)!(L-m-l_N)!} \quad \text{(Eq. 1)}$$
$$(p_{GT\to R}^{low})^{l_R}(p_{GT\to N}^{low})^{l_N}(p_{GT\to R}^{high})^{(m-l_R)}(p_{GT\to N}^{high})^{(L-m-l_N)}.$$

In the above Eq. 1, GT is a specific diploid genotype, D is the sequencing data, L is the sequencing depth at the specific position, or the total number of reads (including high- and low-quality reads) covering this position. $l_R$ is the number of low-quality reads covering the position that support the reference nucleotide R, $l_N$ is the number of low-quality reads covering the position that support the non-reference base N, m is the total number of reads supporting the reference base R. $p^{low}$ GT→R denotes the probability for low-quality reads for the genotype GT to produce the reference base R, which is obtained by looking up the error table 310. An error is assumed to occur only if none of the two nucleotides in the diploid genotype GT is R.

For instance, if GT is "AC", then when R is either 'A' or 'C', an error is not assumed. Only when R is 'G' or 'T', is an error assumed. Similarly, $p^{low}$ GT→N, $p^{high}$ GT→R and $p^{high}$GT→N, respectively denote the error rate for low-quality reads for the genotype GT to produce N, the error rate for high-quality reads for the genotype GT to produce R and the error rate for high-quality reads for the genotype GT to produce N, respectively, and these values are looked up from the corresponding base-wise error tables 308, 310.

At a given location of the reference sequence 202 with base value R, and sequencing data D, a likelihood function L(GT|D, R)=P(D|GT)*P(GT|R) may be used to identify the genotype GT by maximizing (e.g., in some approximate sense) the likelihood function L(GT|D, R). This identification of the genotype GT 5 provides the desired base call.

Depending on the details of the operational setting, embodiments according to the method 100 of FIG. 1 may enable certain characteristic features. First, for data with a multiple quality levels (e.g., ILLUMINA data), the method 100 may take advantage of available knowledge related to the splitting of high- and low-quality reads, and handle them separately. It should be noted that the existence of multiple quality levels in existing sequence data is not conventionally understood or appreciated. Related embodiments may be used to separate sequence data based on quality levels as described in the related U.S. provisional patent application "METHOD AND APPARATUS FOR SEPARATING QUALITY LEVELS IN SEQUENCE DATA AND SEQUENCING LONGER READS," No. 61/898,650, filed Nov. 1, 2013, and which is incorporated herein by reference in its entirety, and related PCT application "METHOD AND APPARATUS FOR SEPARATING QUALITY LEVELS IN SEQUENCE DATA AND SEQUENCING LONGER READS," which is filed on the same date as the present application by an overlapping inventive entity, and which is incorporated herein by reference in its entirety.

Second, the method 100 may employ improved calculations of likelihoods (e.g., prior probabilities and conditional probabilities) by using the SNV rates and error rates estimated from higher depth regions as compared with conventional approaches where a prior probability is assigned without reference to the newly generated sequencing data (e.g., from a general knowledge about how frequently a particular type of SNVs occurs). By contrast, the method 100 may take the higher depth regions of the same sequencing dataset as part of the prior knowledge, and produce much more precise SNV rate parameters which can be used for more accurate prior probability calculations. Similarly, the method 100 may take advantage of the higher depth coverage regions of the same dataset to extract base-wise error rate parameters, which enable more accurate likelihood functions.

Third, the method 100 may more accurately calculate likelihoods of diploid genotypes, thereby leading to improvements in the SNV calling performance. In certain embodiments for testing with multiple datasets (e.g., whole-genome sequencing datasets and exome datasets), the errors produced by embodiments related to the method 100 of FIG. 1 were between 30 and 100 times fewer than other methods, when the sequencing depth (L) is between 10-25, which is typical of common re-sequencing studies.

3. Additional Embodiments

Additional embodiments correspond to systems and related computer programs that carry out the above-described methods.

Figure 6:
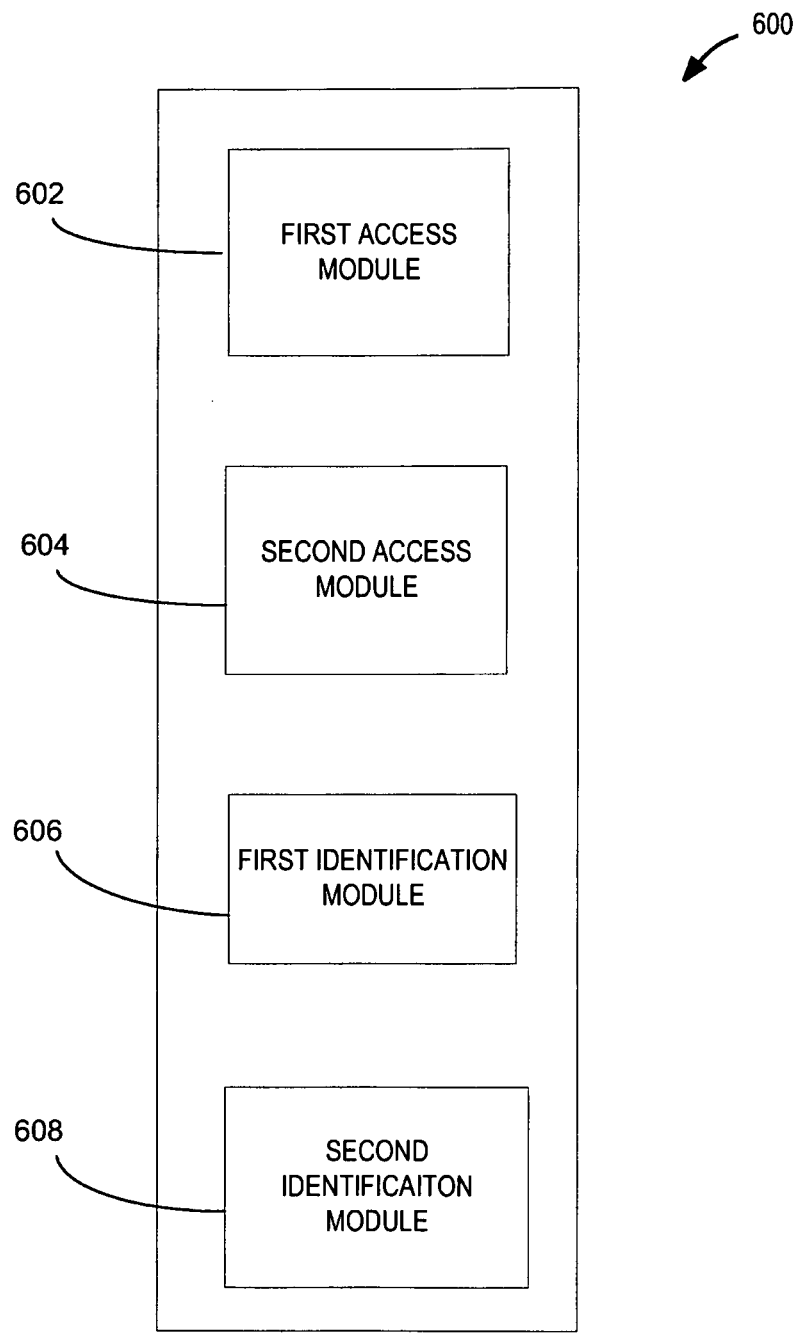
FIG. 6 is a block diagram that shows a schematic representation of an apparatus for an example embodiment.

FIG. 6 shows a schematic representation of an apparatus 600, in accordance with an example embodiment for identifying at least one base call for a target sequence 208. In this case, the apparatus 600 includes at least one computer system (e.g., as in Figure RR) to perform software and hardware operations for modules that carry out aspects of the method 100 of FIG. 1.

In accordance with an example embodiment, the apparatus 600 includes a first access module 602, a second access module 604, a first identification module 606, and a second identification module 608. The first access module 602 operates to access the reference sequence, the reference sequence including a plurality of base values that define the reference sequence. The second access module 604 operates to access a plurality of sequencing reads, each sequencing read including a plurality of base values for a corresponding portion of the target sequence.

The first identification module 606 operates to identify a plurality of high-confidence locations in the sequencing reads, a high-confidence location being identified with a corresponding location in the reference sequence and satisfying a high-confidence condition for using base values of the sequencing reads at the high-confidence location to identify one or more base calls for the target sequence at the high-confidence location. The second identification module 608 operates to identify one or more base calls for the target sequence at a given location not satisfying the high-confidence condition by using base values of the sequencing reads at the high-confidence locations with base values of the sequencing reads at the given location and a base value of the reference sequence at the given location to identify the one or more base calls for the target sequence at the given location.

Additional operations related to the method 100 may be performed by additional corresponding modules or through modifications of the above-described modules.

Figure 7:
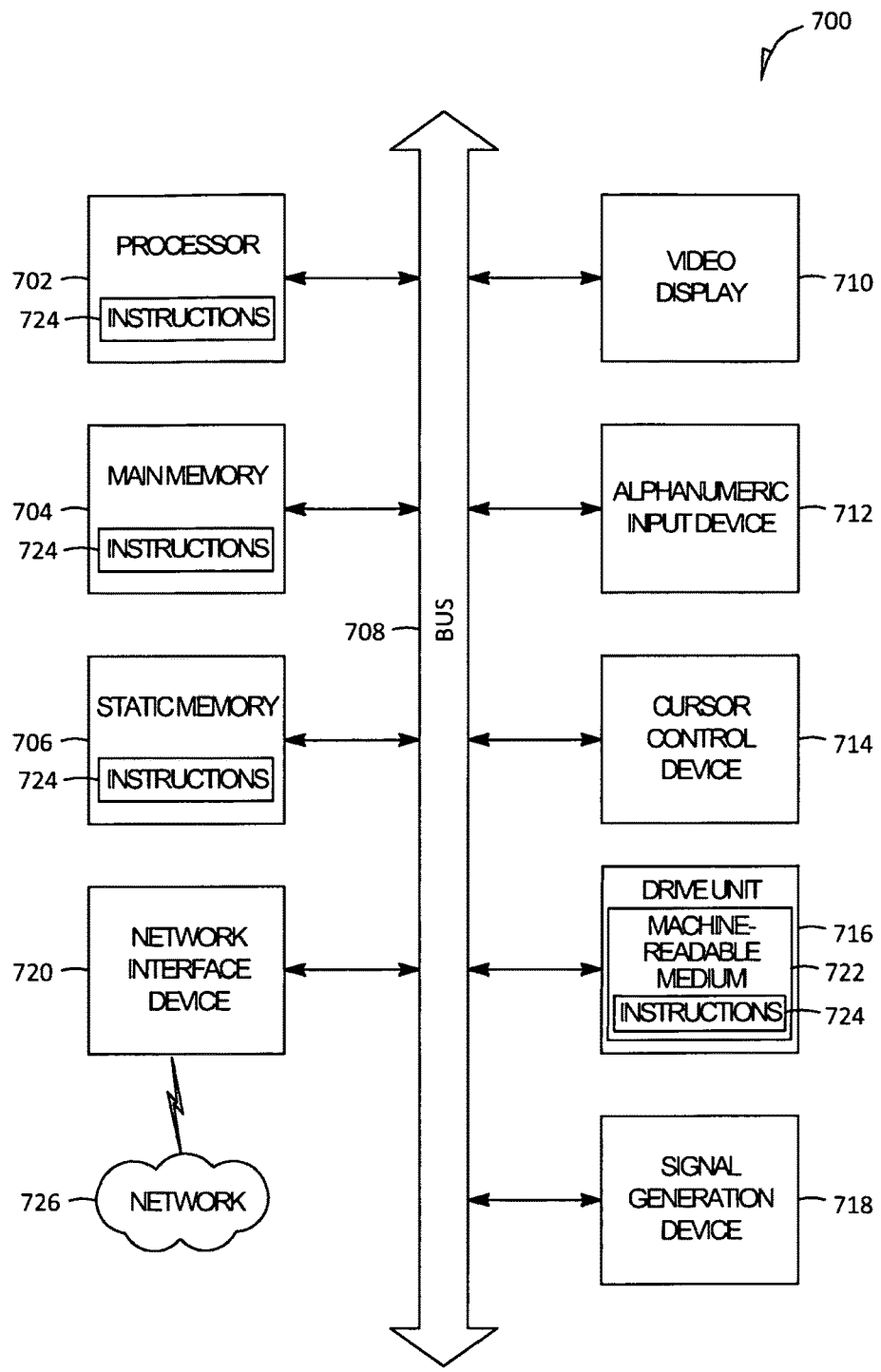
FIG. 7 is a block diagram that shows a computer processing system within which a set of instructions for causing the computer to perform any one of the methodologies discussed herein may be executed.

FIG. 7 shows a machine in the example form of a computer system 700 within which instructions for causing the machine to perform any one or more of the methodologies discussed here may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a personal digital assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 700 includes a processor 702 (e.g., a central processing unit (CPU), a graphics processing unit (GPU) or both), a main memory 704, and a static memory 706, which communicate with each other via a bus 708. The computer system 700 may further include a video display unit 710 (e.g., a liquid crystal display (LCD) or a cathode ray tube (CRT)). The computer system 700 also includes an alphanumeric input device 712 (e.g., a keyboard), a user interface (UI) cursor control device 714 (e.g., a mouse), a disk drive unit 716, a signal generation device 718 (e.g., a speaker), and a network interface device 720.

In some contexts, a computer-readable medium may be described as a machine-readable medium. The disk drive unit 716 includes a machine-readable medium 722 on which is stored one or more sets of data structures and instructions 724 (e.g., software) embodying or utilizing any one or more of the methodologies or functions described herein. The instructions 724 may also reside, completely or at least partially, within the static memory 706, within the main memory 704, or within the processor 702 during execution thereof by the computer system 700, with the static memory 706, the main memory 704, and the processor 702 also constituting machine-readable media.

While the machine-readable medium 722 is shown in an example embodiment to be a single medium, the terms "machine-readable medium" and "computer-readable medium" may each refer to a single medium or multiple media (e.g., a centralized or distributed database, and/or associated caches and servers) that store the one or more sets of data structures and instructions 724. These terms shall also be taken to include any tangible or non-transitory medium that is capable of storing, encoding or carrying instructions for execution by the machine and that cause the machine to perform any one or more of the methodologies disclosed herein, or that is capable of storing, encoding or carrying data structures utilized by or associated with such instructions. These terms shall accordingly be taken to include, but not be limited to, solid-state memories, optical media, and magnetic media. Specific examples of machine-readable or computer-readable media include non-volatile memory, including by way of example semiconductor memory devices, e.g., erasable programmable read-only memory (EPROM), electrically erasable programmable read-only memory (EEPROM), and flash memory devices; magnetic disks such as internal hard disks and removable disks; magneto-optical disks; compact disc read-only memory (CD-ROM) and digital versatile disc read-only memory (DVD-ROM).

The instructions 724 may further be transmitted or received over a communications network 726 using a transmission medium. The instructions 724 may be transmitted using the network interface device 720 and any one of a number of well-known transfer protocols (e.g., hypertext transfer protocol (HTTP)). Examples of communication networks include a local area network (LAN), a wide area network (WAN), the Internet, mobile telephone networks, plain old telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Certain embodiments are described herein as including logic or a number of components, modules, or mechanisms. Modules may constitute either software modules or hardware-implemented modules. A hardware-implemented module is a tangible unit capable of performing certain operations and may be configured or arranged in a certain manner. In example embodiments, one or more computer systems (e.g., a standalone, client or server computer system) or one or more processors may be configured by software (e.g., an application or application portion) as a hardware-implemented module that operates to perform certain operations as described herein.

In various embodiments, a hardware-implemented module (e.g., a computer-implemented module) may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or other programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) may be driven by cost and time considerations.

Accordingly, the term "hardware-implemented module" (e.g., a "computer-implemented module") should be understood to encompass a tangible entity, be that an entity that is physically constructed, permanently configured (e.g., hardwired), or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules can provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation and store the output of that operation in a memory device to which it is communicatively coupled. A further hardware-implemented module may then, at a later time, access the memory device to retrieve and process the stored output. Hardware-implemented modules may also initiate communications with input or output devices and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs)).

4. Conclusion

Although only certain embodiments have been described in detail above, those skilled in the art will readily appreciate that many modifications are possible without materially departing from the novel teachings of this disclosure. For example, aspects of embodiments disclosed above can be combined in other combinations to form additional embodiments. Accordingly, all such modifications are intended to be included within the scope of this disclosure.

What is claimed is:

1. A method of improving accuracy for identifying a base call included in a target sequence produced by a hardware sequencing machine, comprising:
   generating sequencing read data using the hardware sequencing machine;
   retrieving the sequencing read data generated by the hardware sequencing machine, wherein the sequencing read data include a plurality of sequencing reads;
   retrieving a reference sequence that includes a plurality of base values arranged in a particular sequence;
   selecting the plurality of sequencing reads generated by the hardware sequencing machine, wherein
      each sequencing read represents a different portion of the target sequence;
      each sequencing read includes a plurality of base locations arranged in a particular sequence; and
      each base locations is assigned (1) an estimated base value, (2) a Phred quality score that is generated and assigned by the hardware sequencing machine and represents a likelihood that the estimate base value being accurate, and (3) a depth level which represents a total number of sequencing reads, in the plurality of sequencing reads, covering that base location;
   (A) determining base values for high-confidence base locations included in the plurality of sequencing reads, including:
      selecting a first subset of base locations from the plurality of sequencing reads in accordance with a determination that depth levels assigned to the first subset of base locations exceed a predetermined depth level;
      deeming, the first subset of base locations, the high-confidence base locations; and
      determining base values in the high-confidence locations by applying a statistical method to the estimated base values assigned to the high confidence base locations;
   (B) determining base values for low-confidence base locations included in the plurality of sequencing reads, including:
      selecting a second subset of locations out of base values included in the plurality of sequencing reads in accordance with (1) the Phred scores and (2) the depth level assigned to the second subset of locations;
      deeming, the second subset of locations, the low-confidence locations;
   separating the plurality of sequencing reads into (1) a first group of high quality reads and (2) a second group of low quality reads in accordance with whether every location within a sequencing read has an assigned Phred score that is more than above a predefined threshold;
   constructing a target-sequence prediction table based on high confidence locations in the reference sequence, the target-sequence prediction table having (a) a row index for four individual base values (A, C, G, T) that may occur at a location of the reference sequence and (b) a column index for ten diploid combinations (AA, CC, GG, TT, AC, AG, AT, CG, CT, GT) that may occur at that location in one sequencing read of the plurality of sequencing reads;
   constructing a high quality read prediction table based on the first group of high quality reads, the high quality read prediction having (a) a column index that corresponds to the ten diploid combinations that may occur at a location of the target sequence and (b) a row index that corresponds to the four individual base values that may be identified by the hardware sequencing machine for that location;
   constructing a low quality read prediction table based on the second group of high quality reads, the low quality read prediction having (a) a column index that corresponds to the ten diploid combinations that may occur at a location of the target sequence and (b) a column index that corresponds to the four individual base values that may be identified by the hardware sequencing machine for that location;
   selecting a prior probability value from the target-sequence prediction table;
   selecting a conditional probability value from either the high quality read prediction table or the low quality read prediction table; and
   identifying a base call included in the target sequence in accordance with (1) the prior probability value from the target-sequence prediction table and (2) the conditional probability value from either the high quality read prediction table or the low quality read prediction table.

2. The method of claim 1, wherein the hardware sequencing machine is a next-generation sequencing equipment.

3. The method of claim 2, wherein the next-generation sequencing equipment is an ILLUMINA sequencing machine.

4. The method of claim 2, wherein the next-generation sequencing equipment is a high throughput sequencing machine.

5. The method of claim 1 is executed by a computer that is different and separate from the hardware sequencing machine.

6. The method of claim 1, wherein a base value is selected as a high-confidence base value when the depth value associated with the base value is 50 or more.

7. The method of claim 1, wherein identifying a base call included in the target sequence is further in accordance with a Bayesian prediction model, the Bayesian prediction model providing likelihood values that relate the base values of the sequencing reads at the high-confidence locations and the base values of the reference sequence at multiple locations with the one or more base calls for the target sequence at the given location.

8. The method of claim 1, wherein the sequencing read data generated by the hardware sequencing machine have an error rate of at least 1% and base value differences between the target sequence and the reference sequence are less than 1%.

\* \* \* \* \*